(12) United States Patent
Sealfon et al.

(10) Patent No.: US 10,993,877 B2
(45) Date of Patent: May 4, 2021

(54) SYSTEM AND METHOD FOR ANTI-FOAMING NEEDLE ASSEMBLY

(71) Applicant: REPRO-MED SYSTEMS, INC., Chester, NY (US)

(72) Inventors: Andrew I Sealfon, Monroe, NY (US); Siavash Gheshmi, Rocklin, CA (US)

(73) Assignee: Repro-Med Systems, Inc., Chester, NY (US)

( * ) Notice: Subject to any disclaimer, the term of this patent is extended or adjusted under 35 U.S.C. 154(b) by 642 days.

(21) Appl. No.: 15/729,916

(22) Filed: Oct. 11, 2017

(65) Prior Publication Data
US 2018/0116909 A1 May 3, 2018

Related U.S. Application Data

(60) Provisional application No. 62/407,950, filed on Oct. 13, 2016.

(51) Int. Cl.
A61J 1/20 (2006.01)
A61M 5/32 (2006.01)
(Continued)

(52) U.S. Cl.
CPC ........... A61J 1/2082 (2015.05); A61J 1/2013 (2015.05); A61J 1/2027 (2015.05); A61J 1/2037 (2015.05);
(Continued)

(58) Field of Classification Search
CPC ...... A61J 1/2082; A61J 1/2013; A61J 1/2027; A61J 1/2037; A61J 1/2058; A61J 1/2075;
(Continued)

(56) References Cited

U.S. PATENT DOCUMENTS 3,938,520 A 2/1976 Scislowicz et al.
4,787,898 A 11/1988 Raines
(Continued)

OTHER PUBLICATIONS

PCT International Search Report for International Application PCT/US2017/056210, search report data dated Jan. 19, 2018 (dated Jan. 19, 2018).

Primary Examiner — Philip R Wiest
(74) Attorney, Agent, or Firm — Daniel W. Roberts; Law Offices of Daniel W. Roberts, LLC

(57) ABSTRACT

Provided is a system and method for an anti-foaming needle assembly for avoiding foam generation when extracting a liquid from a vessel having a chamber with a bottom and opposite thereto an opening sealed with a penetrable and re-sealable stopper providing an inner surface above the chamber. More specifically, the anti-foaming needle assembly includes a needle base having: a first end and opposite thereto a second end and a sidewall there between, the second end structured and arranged for temporary connection to a syringe having a barrel and a plunger; a first needle having a hollow shaft and a first length extending from the first end to provide an open distal end above the first end, the first needle having a second end vented through the sidewall; and a second needle having a hollow shaft and a second length extending from the first end generally parallel to the first needle to provide, when inverted, a distal end above the first end and below the distal end of the first needle, the second needle having a second end in fluid communication with the second end of the needle base. An associated method of use is also provided.

28 Claims, 5 Drawing Sheets

(51) Int. Cl.
*A61M 5/34* (2006.01)
*A61M 5/38* (2006.01)
*A61M 5/31* (2006.01)

(52) U.S. Cl.
CPC ........... *A61J 1/2058* (2015.05); *A61J 1/2075* (2015.05); *A61J 1/2096* (2013.01); *A61M 5/3298* (2013.01); *A61M 5/345* (2013.01); *A61M 5/347* (2013.01); *A61M 5/385* (2013.01); *A61M 2005/3123* (2013.01)

(58) Field of Classification Search
CPC .... A61J 1/2096; A61M 5/3298; A61M 5/345; A61M 5/347; A61M 5/385; A61M 2005/3123
See application file for complete search history.

(56) References Cited

U.S. PATENT DOCUMENTS

| | | | |
|---|---|---|---|
| 5,472,434 | A | 12/1995 | Lechleiter |
| 7,288,078 | B2 | 10/2007 | Fitsgerald |
| 7,938,454 | B2 | 5/2011 | Buchanan et al. |
| 8,167,864 | B2 | 5/2012 | Browne |
| 8,562,582 | B2 | 10/2013 | Tuckwell et al. |
| 8,702,129 | B2 | 4/2014 | Bilstad et al. |
| 2008/0265561 | A1 | 10/2008 | Buchanan et al. |
| 2009/0005753 | A1 | 1/2009 | Browne |
| 2010/0030181 | A1 | 2/2010 | Helle et al. |
| 2010/0076397 | A1 | 3/2010 | Reed et al. |
| 2013/0046270 | A1 | 2/2013 | Foshee et al. |
| 2014/0230952 | A1 | 8/2014 | Higuchi et al. |
| 2015/0320642 | A1* | 11/2015 | Fangrow ............... A61J 1/22 137/798 |

\* cited by examiner

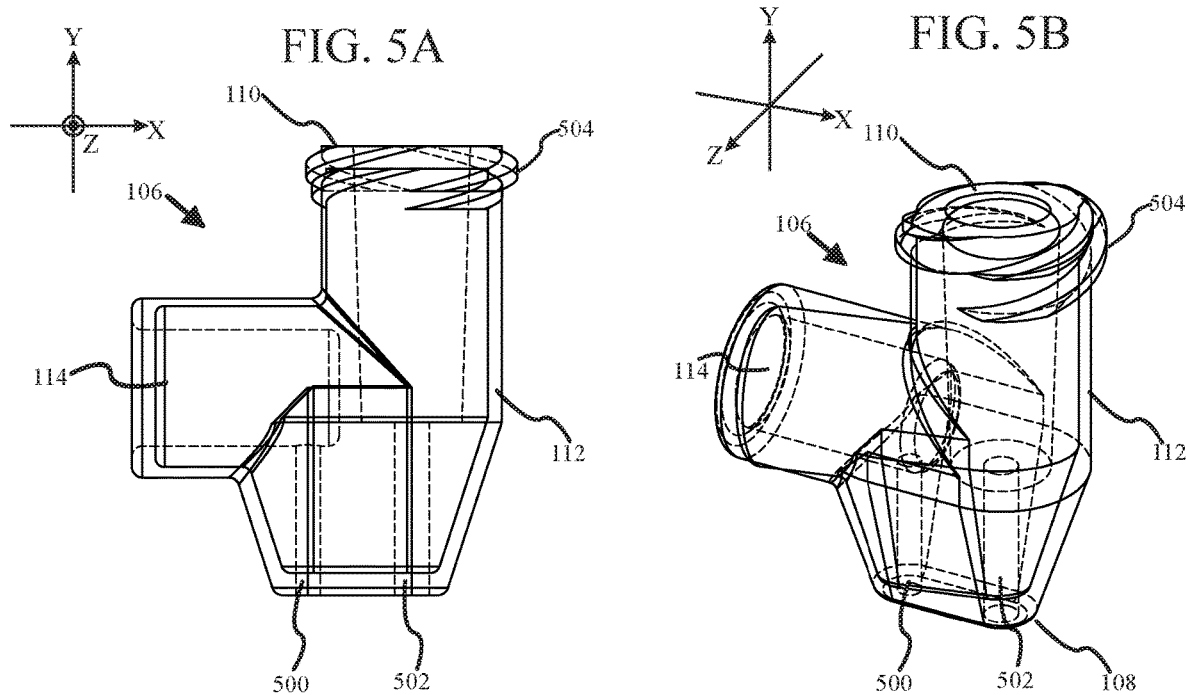
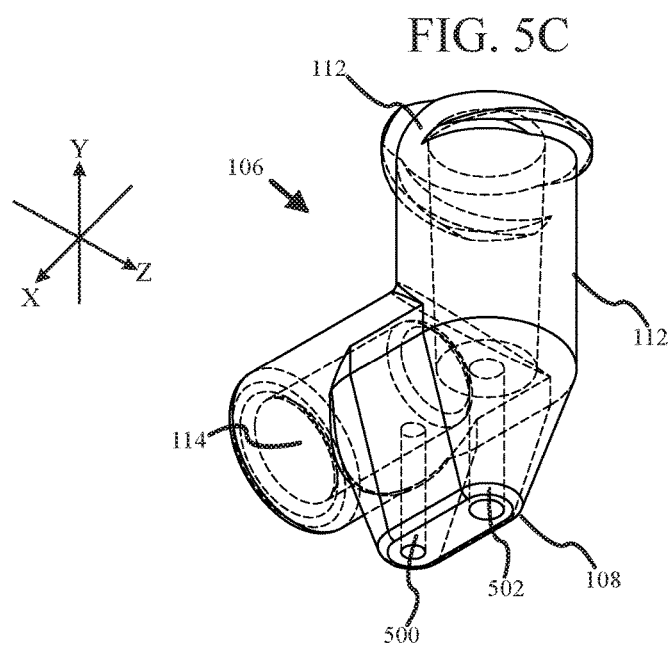

SYSTEM AND METHOD FOR ANTI-FOAMING NEEDLE ASSEMBLY

CROSS REFERENCE TO RELATED APPLICATIONS

This application claims the benefit under 35 U.S.C. § 119(e) of U.S. Provisional Application No. 62/407,950 filed Oct. 13, 2016 and entitled SYSTEM AND METHOD FOR ANTI-FOAMING NEEDLE ASSEMBLY, the disclosure of which is incorporated herein by reference.

FIELD OF THE INVENTION

The present invention relates generally to devices for extracting liquid, from vials to syringe, that avoid the common foaming that occurs as air bubbles through the liquid. Foaming is highly undesirable as foam is not easily drawn into the syringe, thus resulting in a loss of at least some of the liquid that remains unobtainable in the vial, a costly and wasteful issue.

BACKGROUND

Although pre-loaded syringes are used in some applications, it is far more common for medications to be provided in pre-measured vials. Typically, a vial is a sterile container, commonly glass, which has a penetrable and re-sealable stopper that acts to contain the liquid drug solution safely within while permitting a needle to pass through for extraction.

Medication within the vial is typically provided in one of two forms, the first is as a liquid drug solution ready for extraction. Due to shipping costs, weight, and potentially the longevity of the medication, the second form is dry—such as a powder, which is reconstituted by injecting a measured amount of water or other liquid into the vial to provide a drug solution.

For either option, the same issue of foaming may occur. As the vial contains the desired liquid and is sealed, the general method of loading a syringe is to direct the needle of a syringe through the rubber stopper and then draw back on the plunger of the syringe to create suction within the chamber of the syringe, and correspondingly suction the liquid through the needle.

As the liquid is drawn into the syringe the pressure drops within the syringe and air may be sucked into the vial around the needle. Moreover, while the rubber seal is sufficient to prevent liquid leaking out around the needle, the pressure differential and flexible nature of the rubber stopper may permit air to be sucked in.

As the vial is typically inverted during extraction, the rubber seal is then at the lowest point of the vial. Accordingly, any air entering the vial around the needle must percolate through the liquid within the vial—thus creating the issue of bubbling and foaming. As more and more liquid is extracted, more and more air will be sucked in and more foaming may occur.

It should be noted that in some cases the seal between the needle and the rubber seal is so tight that air will not enter, but without the introduction of air, it may be all but impossible for the user to withdraw the desired amount of drug solution.

Of course, one recommended option is to draw into the syringe a volume of air equal to the volume of drug solution to be withdrawn from the vial, insert the needle through the stopper, invert the vial and inject the air into the vial and then withdraw the drug solution. For the typical end user patient this is impractical. If too much air is injected into the vial, the drug solution may be forced out around the needle. If the air is injected through the drug solution and not above it, then again bubbling and foaming may occur.

If the medication is for an infusion treatment where it is likely the entire vial is to be used in one treatment, then this process must be repeated many times, and with each repeated process the same issues of foaming and potential loss occur. In addition, the repeated back and forth of injected air and suctioning of the drug solution will also most likely add bubbles to the drug solution within the syringe, which is also undesirable.

To facilitate the introduction of air into the vial during the extraction process, devices known as Mini-Spike® by Braun Medical Inc. have been developed. In general, these devices are in essence a structure operating as a vented needle, an example of which can be found in U.S. Pat. No. 4,787,878 to Rains and entitled Vented Needle with Sideport. More specifically, Rains teaches a main body having two ports at right angles to one another—one to conduct liquid and the other to conduct air. These ports each terminate in the needle tip providing a continuous slanted end structure. The port for air is slightly above the port for liquid, but the difference in height is appreciably immaterial.

Although effective at introducing air into the vial during extraction of the drug solution, because the air and fluid ports are effectively adjacent to each other and both are within the drug solution during extraction, the improved flow of air provided by the air port delivers air directly into the drug solution and results in even greater bubbling and foaming then does air seeping in around a non-vented needle.

The earlier reference of Scislowicz, U.S. Pat. No. 3,938,520 also provides two ports, in this case on their side of a piercing tip. As with the reference Rains, the Scislowicz device has the air port and the liquid port effectively next to each other, and as such both are disposed within the liquid during extraction from the vial. Thus, as with the more contemporary Rains device, the Scislowicz device again is highly effective at generating bubbling and foaming during the extraction process.

Moreover, whether of the Scislowicz, Rains, Mini-Spike® or generic style equivalent, these types of vented needles permit the development of foam within the vial because during extraction the air delivery point is within the drug solution itself.

Hence, there is a need for a method and system for an anti-foam needle assembly, able to remove drug solution from a vial that is capable of overcoming one or more of the above identified challenges.

SUMMARY OF THE INVENTION

Our invention solves the problems of the prior art by providing novel systems and methods for an anti-foam needle assembly.

In particular, and by way of example only, according to one embodiment of the present invention, provided is a method of avoiding foam generation when extracting a liquid from a hollow vessel suitable for the containment of liquids, the vessel having a chamber with a bottom and opposite thereto an opening sealed with a penetrable and re-sealable stopper providing an inner surface above the chamber, including: inserting a first needle having a hollow shaft through the penetrable and re-sealable stopper to dispose a distal end of the first needle adjacent to the bottom of the chamber, a second end of the first needle remaining open outside the chamber; inserting a second needle having a hollow shaft through the penetrable and re-sealable stopper to dispose a distal end of the second needle adjacent to the inner surface, a second end of the second needle connected to a syringe having a barrel with a plunger; inverting the vessel, the distal end of the first needle now disposed adjacent to the upper most inner surface of the chamber; and activating the plunger to draw the liquid from the vessel through the second needle and into the barrel of the syringe, the first needle permitting air to be delivered into the vessel above the liquid being dispensed so as to minimize foaming of the liquid during extraction.

For another embodiment, provided is an anti-foaming needle assembly for avoiding foam generation when extracting a liquid from a hollow vessel suitable for the containment of liquids, the vessel having a chamber with a bottom and opposite thereto an opening sealed with a penetrable and re-sealable stopper providing an inner surface above the chamber, including: a needle base having: a first end and opposite thereto a second end and a sidewall there between, the second end structured and arranged for temporary connection to a syringe having a barrel and a plunger; a first needle having a hollow shaft and a first length extending from the first end to provide an open distal end above the first end, the first needle having a second end vented through the sidewall; and a second needle having a hollow shaft and a second length extending from the first end generally parallel to the first needle to provide a distal end above the first end and below the distal end of the first needle as the first length is at least twice the second length, the second needle having a second end in fluid communication with the second end of the needle base; wherein the first length is pre-selected to place the distal end of the first needle proximate to the bottom of the chamber and the second length is pre-selected to place the distal end of the second needle within the chamber and proximate to the re-sealable stopper.

And for yet another embodiment, provided is an anti-foaming needle assembly for avoiding foam generation when extracting a liquid from a vessel suitable for the containment of liquids, the vessel having a chamber with a bottom and opposite thereto an opening sealed with a penetrable and re-sealable stopper providing an inner surface above the chamber, including: a needle base having: a first end and opposite thereto a second end and a sidewall there between, the second end structured and arranged for temporary connection to a syringe having a barrel and a plunger; a compound needle assembly having an shaft extending from the first end of the base, to a distal end above the base, the shaft enclosing a first and second fluid channel; the first channel in fluid communication with a vent disposed in the sidewall of the needle base and terminating as at least one first opening at the distal end of the shaft; and the second channel in fluid communication with the a second end of the base and terminating as a second opening along the shaft before the distal end; wherein the shaft has a length pre-selected to place the distal end proximate to the bottom of the chamber and the opening along the shaft at a location pre-selected to place the opening within the chamber and proximate to the re-sealable stopper.

BRIEF DESCRIPTION OF THE DRAWINGS

FIGS. 5A, 5B and 5C are illustrations showing side and perspective views of the needle base 106 of the Anti-Foaming Needle Assembly shown in FIG. 1A.

DETAILED DESCRIPTION

Before proceeding with the detailed description, it is to be appreciated that the present teaching is by way of example only, not by limitation. The concepts herein are not limited to use or application with a specific system or method for an anti-foaming needle assembly. Thus, although the instrumentalities described herein are for the convenience of explanation shown and described with respect to exemplary embodiments, it will be understood and appreciated that the principles herein may be applied equally in other types of systems and methods involving anti-foaming needle assembly and method to remove drug solutions from vials without foaming the drug solution.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Figure 1A:
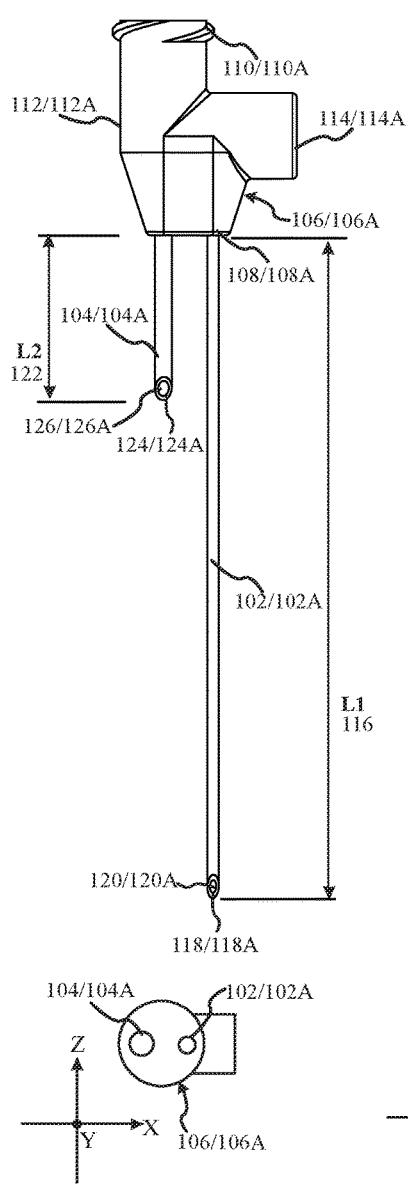
FIGS. 1A, 1B and 1C present side and bottom views showing Anti-Foaming Needle Assemblies in accordance with varying embodiments.
Figure 1B:
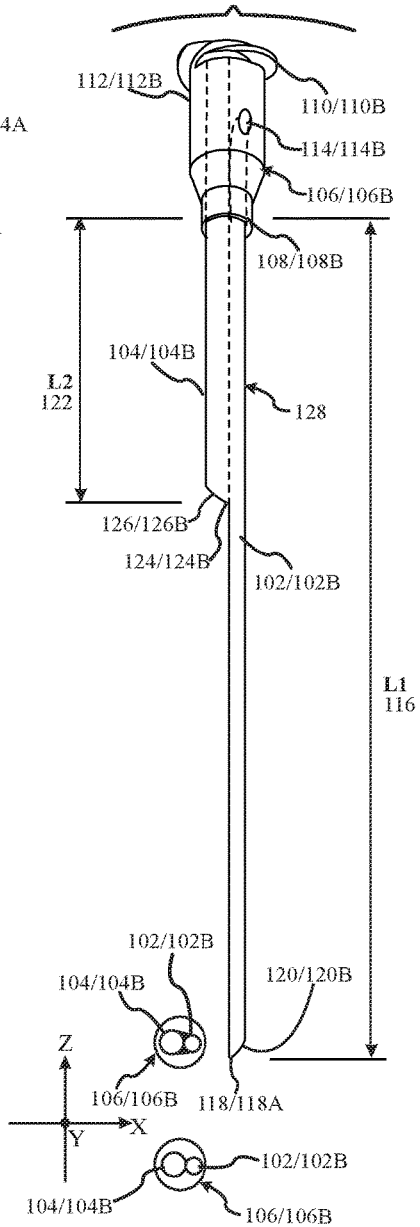
Figure 1C:
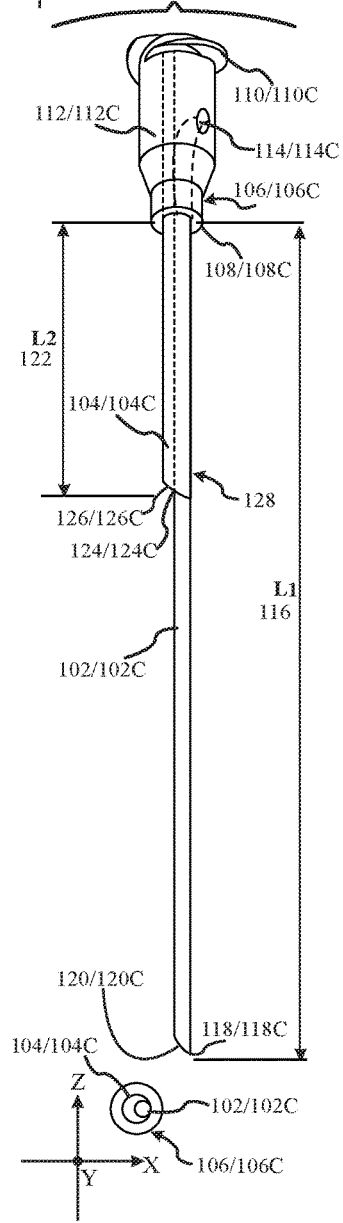

Turning now to FIG. 1, and more specifically FIGS. 1A, 1B and 1C, shown in the annotated drawing are three variations of an Anti-Foaming Needle Assembly, hereinafter AFNA 100 according to varying embodiments of the present invention. As is further set forth below, in general, AFNA 100 comprises a first needle 102 and a second needle 104 extending in parallel from a common base 106. The base 106 has a first end 108 and a second end 110 and a sidewall 112 there between. The first needle 102 is coupled to a vent 114 in the base 106. The second needle 104 is in fluid communication with the second end 110 of the base 106 which is structured and arranged to be coupled to a syringe.

Beginning on the far left, FIG. 1A, is Variation #1 for AFNA 100A, having two distinctly separate needles—first needle 102A and second needle 104A. In the middle FIG. 1B depicts Variation #2 for AFNA 100B, having two needles disposed adjacent to one another along one side—first needle 102B and second needle 104B. On the far right is FIG. 1C showing Variation #3 for AFNA 100C having two needles sleeved together, the second needle 104C sleeved about the first needle 102C.

To facilitate the description of systems and methods for this AFNA 100, the orientation of AFNA 100 as presented in the figures is referenced to the coordinate system with three axes orthogonal to one another as shown in FIG. 1. The axes intersect mutually at the origin of the coordinate system, which is chosen to be the center of the AFNA 100, however the axes shown in all figures are offset from their actual locations for clarity and ease of illustration.

For each Variation #1, #2 and #3, the base 106 of the AFNA 100 has a first end 108 and opposite thereto a second end 110 and a sidewall 112 between the ends. The second end 110 is structured and arranged for temporary connection to a syringe having a barrel and a plunger (see FIGS. 4A and 4B). Moreover, in at least one embodiment, the second end 110 is a luer connector.

As shown, the needles all extend from the base's first end 108. Further, it will be appreciated that in Variations #1 100A, #2 100B and #3 100C the first and second needles—102A/104A, 102B/104B and 102C/104C respectively—are generally parallel to one another as well. In addition, it will be appreciated that for at least one embodiment, such as the AFNA 100A of FIG. 1A, the first needle 102A and the second needle 104A are indeed distinct separate structures extending from the base 106A. Moreover, there is physical space between the first needle 102A and the second needle 104A as they extend away from the base 106.

For at least one alternative embodiment, such as the AFNA 100B of FIG. 1B or AFNA 100C of FIG. 1C, the first needle 102C/B and the second needle 104C/B are at least partially in side contact with one another, if not integrated as a combined structure.

The first needle 102 has a hollow shaft and has a first length, L1 116, such that it extends from the first end 108 of the base 106 to provide a distal end 118 with at least one opening 114 proximate thereto. As the first needle 102 is hollow, the second end is vented through a vent opening, e.g. vent 114, in the sidewall 112 of the base 106. For yet an alternative embodiment the vent 114 could be disposed in the first end 108, or even the second end 110 of the base 106, however, for at least one embodiment being disposed in the sidewall 112 is simpler for manufacturing, and as discussed further below, may facilitate embodiments where the first needle 102 may be pressed further back into the base 106.

For at least one embodiment, the first needle 102 is fitted with an air filter, such as by disposing a filter within the vent 114. In addition, for at least one embodiment, the first needle 102 may be gated by a one-way valve, permitting air to pass through and into the vent 114 and thus travel out the at least one opening 114 in the distal end 118 of the first needle 102, but not permitting air or liquid to pass back through the first needle 102 and then out the vent 114.

The second needle 104 likewise also has a hollow shaft and a second length, L2 122, extending from the first end 108 of the base 106 and generally parallel to the first needle 102 to provide, when inverted, a distal end 124 above the base 106 and below the distal end 118 of the first needle 102. There is at least one opening 126 proximate to the distal end 124 of the second needle 104.

For yet another embodiment, similar to Variation #3 100C of FIG. 1C, an AFNA 100 may be provided as an even more fully integrated compound needle 128 that tapers about a quarter to a third, or half of the way up its length from a dual channel structure providing both the inner channel for liquid as with the second needle 104 and the air passage channel of the first needle 102, to a needle structure that is equivalent to just the first needle 102, just above one or more distal openings to the liquid channel of the first needle 102 portion of the compound needle 128 structure. Such a compound needle 128 structure may be desired in some embodiments as it effectively has only one pointed tip.

As is clearly apparent in FIG. 1 and the drawings of Variations #1 100A, #2 100B and #3 100C, the length of the first needle 102, e.g., L1 116, is considerably longer then the length of the second needle 104, e.g. the L2 122. It will be understood and appreciated that its key element is the relative difference between the distal end 118 of the first needle 102 and the distal end 124 of the second needle 104, and more specifically the relative difference between the opening 120 proximate to the distal end 116 of the first needle and the opening 126 proximate to the distal end 124 of the second needle 104.

Moreover, for a given vial of liquid, there is an internal dimension between the inside bottom of the vial chamber and the inside surface of the re-sealable stopper. The relative difference between the First Length and the Second Length is pre-selected so as to place the distal end 116 of the first needle 102 proximate to the bottom of the vial chamber and place the distal end 124 of the second needle 104 also within the vial and proximate to the inner surface of the re-sealable stopper.

By such a configuration, when an embodiment of AFNA 100 affixed to a syringe is directed through the re-sealable stopper, the distal end 116 of the first needle 102 will be proximate the bottom of the chamber and the distal end 124 of the second needle 104 will be proximate to the inside surface of the re-sealable stopper. When the vial is then inverted, the liquid will thus be directly around and above the distal end 124 of the second needle 104 while the distal end 116 of the first needle 102 will be above the liquid and thus within the air or other gas bubble above the liquid and within the vial.

As the plunger is drawn backward creating a suction within the chamber of the syringe, air will pass from the opening 120 proximate to the distal end 116 of the first needle 102 and into the vial, however as the opening 120 proximate to the distal end 116 is out of the liquid (e.g. it is above the liquid within the air pocket within the vial), no foaming will occur.

Moreover, as will be further explained below with reference to the accompanying figures, the first needle 102 is intended to facilitate the passage of air into the vial at a point well above the opening 126 at the distal end 124 of the second needle 104 which draws the liquid out of the vial.

Figure 2A:
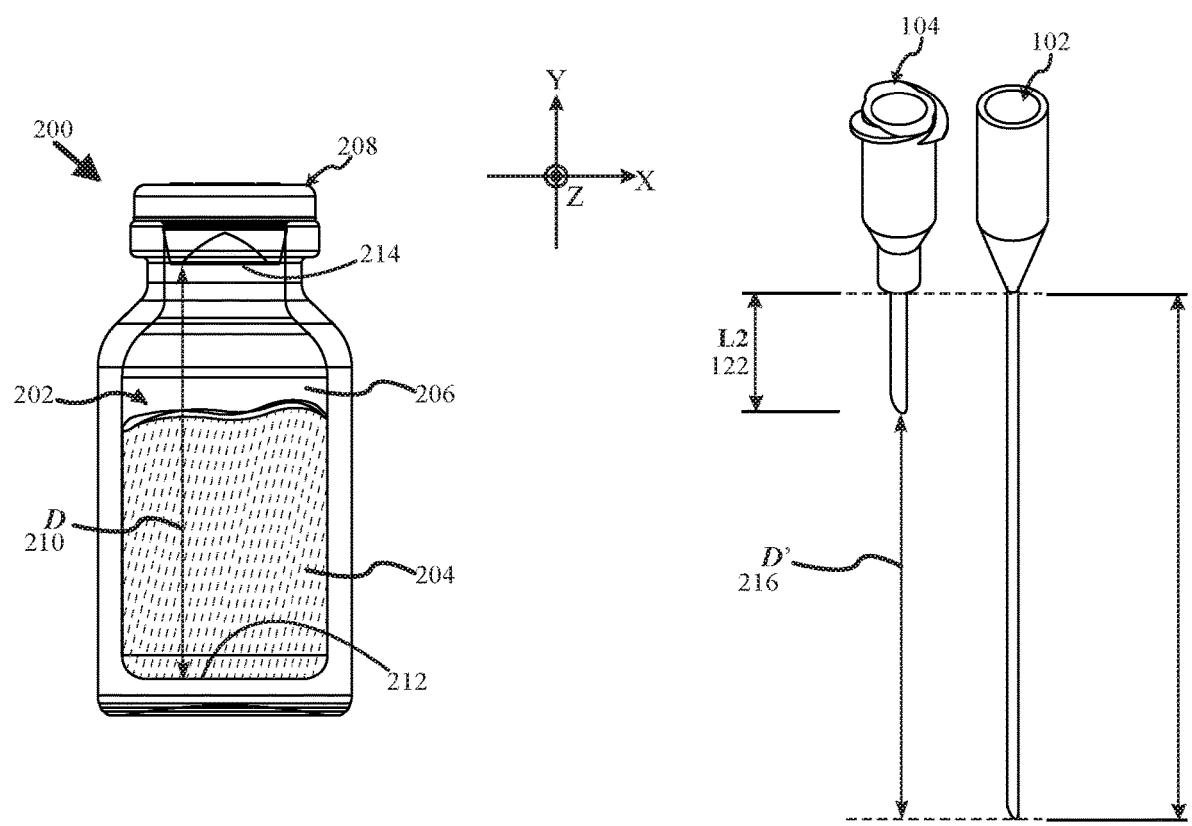
FIG. 2A is an illustration of a vial containing a liquid and two distinct needles of significantly different length in accordance with varying embodiments of the present invention.

This may be further appreciated with respect to FIG. 2A, showing an exemplary vial 200, and two separate needles representing the first needle 102 and the second needle 104. As may be appreciated the vial 200 has a chamber 202 and a liquid 204 within the chamber 202. When sitting upright, there is an air gap or air pocket 206 above the liquid 204. The liquid 204 has been shown with a slight wave at the top, as if the vial 200 had just been moved, to facilitate easier appreciation of the liquid 104. It is understood and appreciated that "air" is not strictly a limitation to breathable air, but refers to the gas in this space which may be normal air, sanitized air, another gas or combination of gases.

A re-sealable stopper 208 is affixed to the vial 200 which permits a needle to be inserted into the vial 200, which is the traditional way to withdraw the liquid 204 from the vial 200. As is also shown, there is a dimension D 210 between the bottom 212 of the chamber 202 and the inner surface 214 of the re-sealable stopper 208.

As shown, the first needle 102 and the second needle 104 have their bases aligned such that the difference in length between them is effectively the dimension D' 216. In varying embodiments D' 216 is equal to or slightly less than D 210.

Moreover, for at least one embodiment, D' 216 is at least 50% of D 210. Further still, for at least one embodiment, D' 216 is at least 80% of D 210. Moreover, for at least one embodiment D' 216 is selected to be between D 210 and 25% of D 210.

Figure 2B:
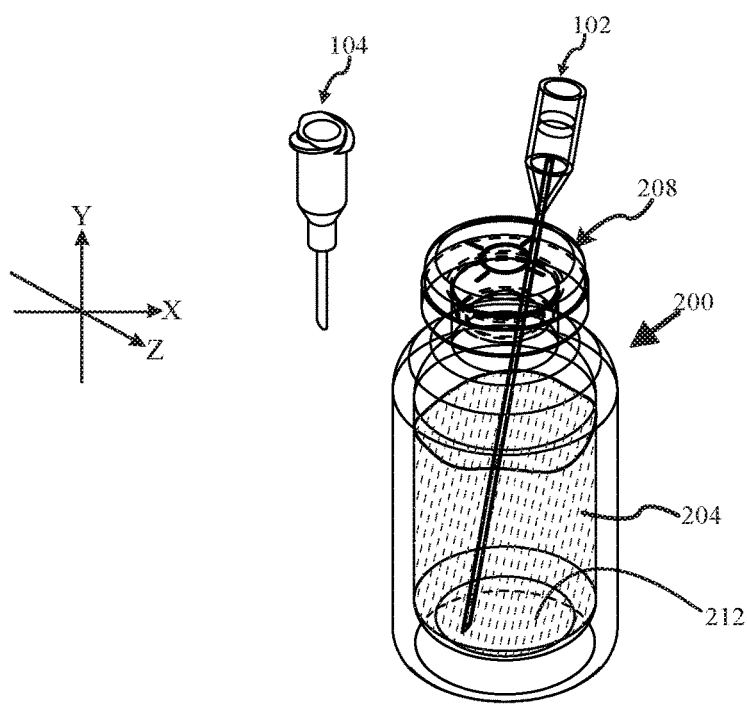
FIG. 2B is an illustration showing the longer needle, first needle, disposed through the re-sealable stopper of the vial and extending to the bottom of the vial, the second needle shown adjacent to the top of the vial for comparison depth of penetration comparison in accordance with varying embodiments of the present invention.

As shown in FIG. 2B, the first needle 102 has been inserted through the re-sealable stopper 208 and the distal end 118 of the first needle 102 is resting upon the bottom 212 of the chamber 212. In contrast, it is clear that the second needle 104 which has been placed next to the vial 200 will only extend partially into the chamber 202 when it is directed through the re-sealable stopper 208 as shown in FIGS. 3A and 3B.

Figure 3A:
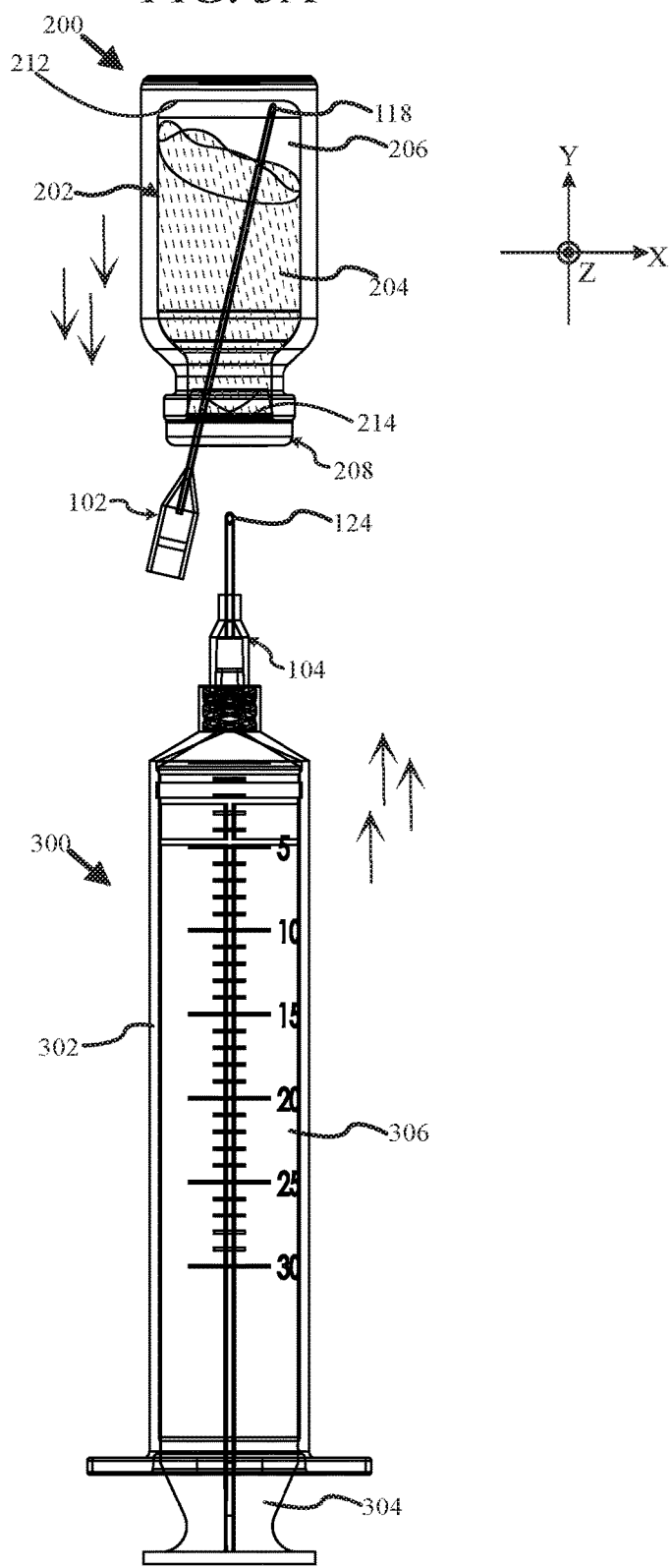
FIGS. 3A and 3B are illustrations showing the use of the two separate needles shown in FIGS. 2A and 2B for foamless extraction of liquid from the vial in accordance with varying embodiments of the present invention.

In FIG. 3A the vial 200 with the first needle 102 inserted is shown inverted and positioned above the second needle 104 affixed to a syringe 300 having a barrel 306 and a plunger 304 which cooperatively interact to define a chamber 302 within the syringe 300. As the vial 200 has now been inverted, it is clear that the distal end 118 of the first needle 102 is in the air pocket 206 within the chamber 202 of the vial 200 as the distal end 118 of the first needle 102 is adjacent to the bottom 212 of the chamber 202.

Figure 3B:
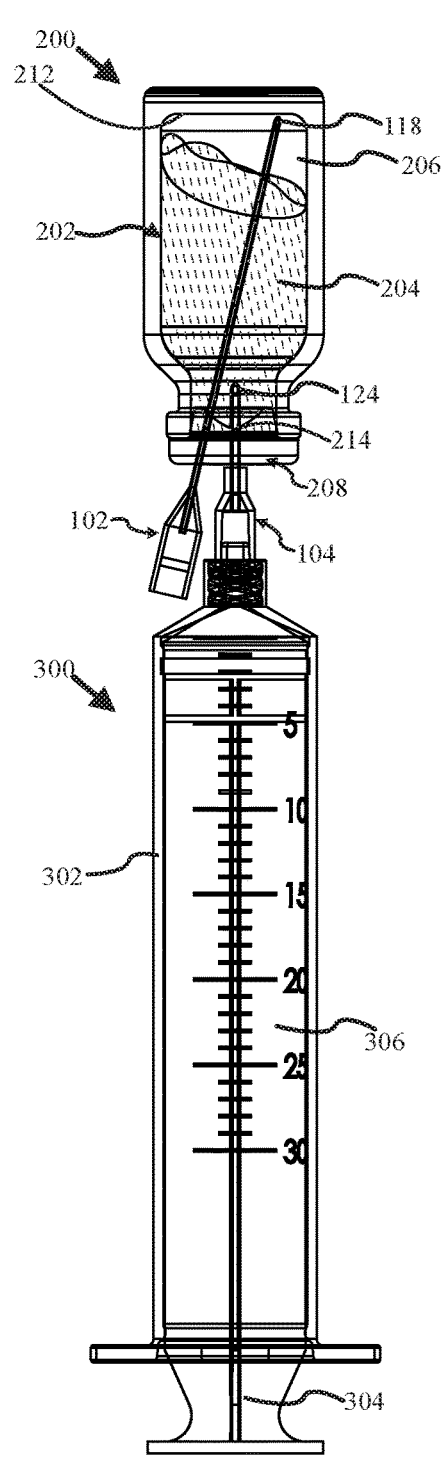

The vial 200 and the second needle 104 are then brought together as shown in FIG. 3B. Now, the distal end 124 of the second needle 104 is appreciated to be proximate to the inner surface 214 of the re-sealable stopper 208. As such, when the plunger 304 is retracted, liquid 204 will be drawn through the second needle 104 and into the chamber 306 of the syringe 300 as air travels through the first needle 102 into the vial 200 chamber 202 to a release point that is well above the liquid 204 in the chamber 202. As such, no air bubbles through the liquid 204 and foaming is advantageously avoided.

While certainly effective to avoid the issue of foaming, the use of two separate and distinct needles, e.g. separate first needle 102 and separate second needle 104, may not be ideal in all situations. As such, varying embodiments of AFNA 100 provide the anti-foaming advantage of two distinct needles without requiring the user to safeguard both needles, distinguish between which needle should be attached to the Syringe and which should not, and manipulate the orientation of the first needle 102 so as to allow proper placement of the second needle 104.

Figure 4A:
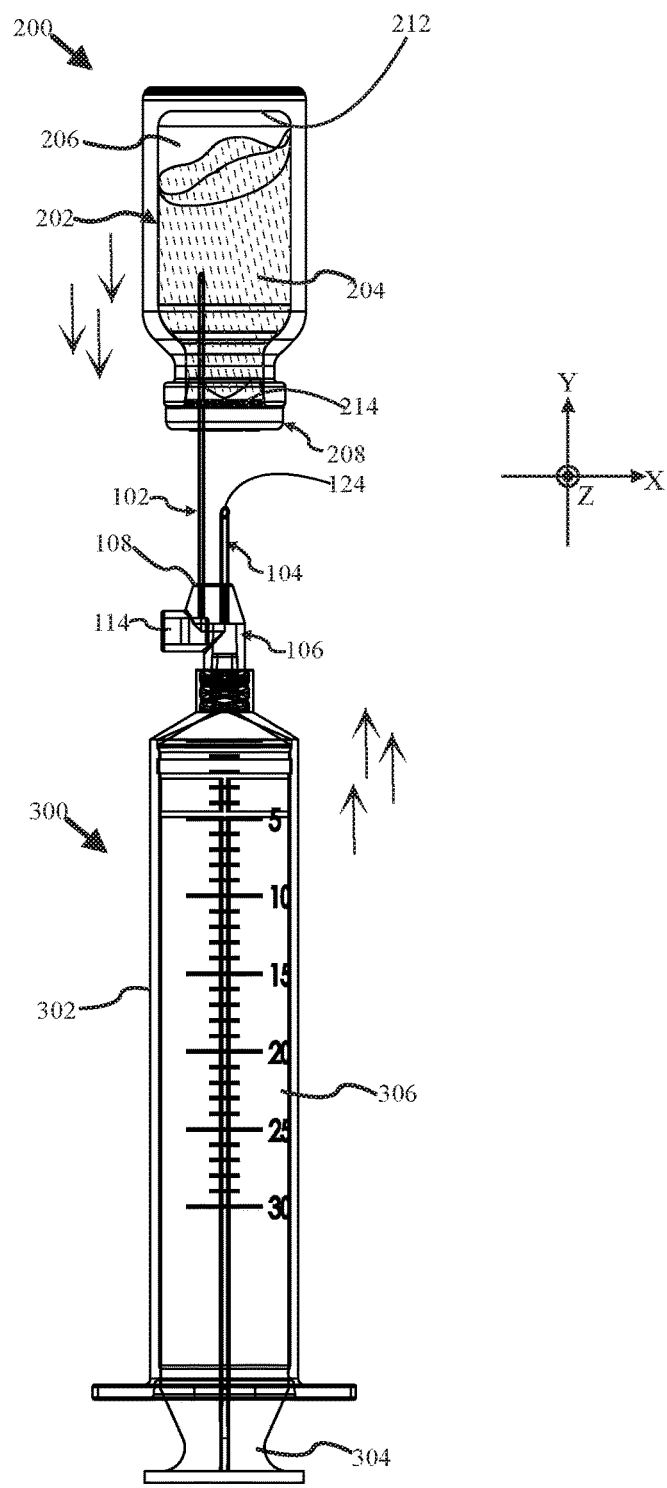
FIGS. 4A and 4B are illustrations showing an anti-foaming needle assembly as shown in FIG. 1A for foamless extraction of liquid from the vial in accordance with varying embodiments of the present invention.
Figure 4B:
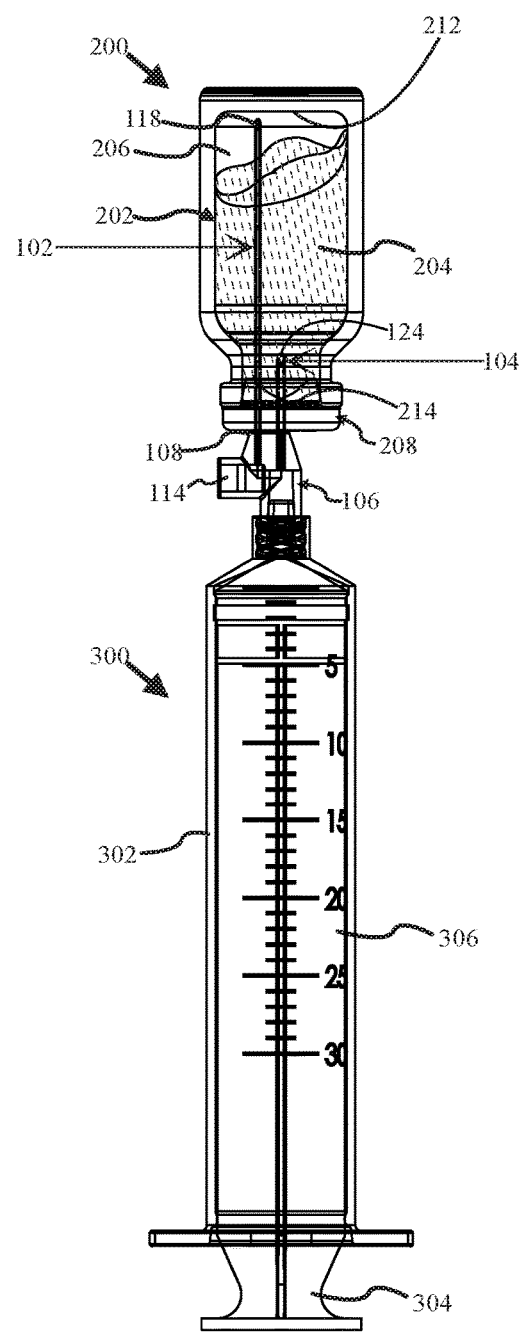

FIGS. 4A and 4B show an embodiment of AFNA 100 corresponding to Variation #1 100A shown in FIG. 1A noted above. As shown in FIGS. 4A and 4B, the AFNA 100 has been attached to a syringe 300. In advantageous contrast to the two needle process shown in FIGS. 3A and 3B, here the operator is only required to manipulate one assembly and the vial 200.

Moreover, attached to the syringe 300, the operator has a firm and large object to grasp and therefore may also enjoy an easier experience of directing the first needle 102 through the re-sealable stopper 208 and then seating the second needle 104 through the re-sealable stopper 208 as well. More specifically, the first end 108 of the base 106 has now encountered the re-sealable stopper 208 and further motion of either the first needle 102 or the second needle 104 further into the vial 200 is effectively prevented.

For at least one embodiment the length of the second needle 104 is preselected so as to be sufficient to pass thorough the re-sealable stopper 208 and place the distal end 124 of the second needle 104 proximate to the inner surface 214 of the re-sealable stopper 208. For at least one embodiment, the base 106 may have a generally flat first end 108 such that the operator may confirm proper placement of the AFNA 100 by abutting the first end 108 against the outer surface of the re-sealable stopper 208.

As is suggested by the illustrations, the first needle 102 may be a finer gage needle then the second needle 104, as it's principle function is simply the passage of air from the outside, through the re-sealable stopper 208 and the liquid 204 to a point inside the vial 200 that is above the liquid 204 when the vial 200 is inverted as shown. In addition, in varying embodiments, the first needle 102 may be at least partially flexible, such that it may bend if, or when, encountering the bottom 212 of the chamber 202.

For at least one embodiment, the length L1 116 of the first needle 102 is sufficient to make contact with bottom 212 of the chamber 202. For at least one alternative embodiment, the length L1 116 of the first needle 102 is selected to be shorter than the internal dimension shown as D 210 in FIG. 2A, such that the distal end 118 of the first needle 102 is proximate to the bottom 212 of the chamber 202 but does not necessarily make contact.

For yet another embodiment, the base 106 to which the first needle 102 is mounted, permits the first needle 102 to slide back down into the base 106 in the event that the first needle 102 makes contact with the bottom 212 of the chamber 202 as the AFNA 100 is engaged to seat the second needle 104 through the re-sealable stopper 208.

For still another embodiment, the first needle 102 is a telescoping structure comprising at least two sections which have been slip fit together in a snug relationship. Again, the snug fit may be sufficient to overcome the resistance of the re-sealable stopper 208, but in the event that the distal end 118 of the first needle 102 makes contact with the bottom 212 of the chamber 202, the sections will slide together to take up excess length L1 116 and permit the second needle 104 to be seated through the re-sealable stopper 208.

In still other embodiments, the telescoping structure may initially be in a compacted stowed position. When the telescoping structure is inserted through the re-sealable stopper 208 it may be extended from the stowed position towards the length L1 116. Again, the telescoping structure may be structured and arranged to be just short of reaching the bottom 212 of the chamber 202, or the concentric elements may stop further expansion once resistance from the bottom 212 of the chamber 202 is encountered.

For yet another embodiment, such as variations of AFNA 100 as shown in FIG. 1B (AFNA 100B) and FIG. 1C (AFNA 100C) where the needle structure is a compound needle structure, the first needle 102 may be held in a compressed state at about the same length as the second needle 104. This may be accomplished at least in part by a protective cover disposed over both the first needle 102 and the second needle 104. For such an embodiment, the first needle 102 may not be sharp, such that it does not cut through the cover. However, when AFNA 100 with the cover in place is disposed against the re-sealable stopper 208, the second needle 104 may be sharp and as the cover compresses back towards the base 106, the first needle 102 and second needle 104 will pass through the protective cover and the re-sealable stopper 208. Now, unrestrained, the first needle 102 can telescopically expand toward the length L1 116.

In addition, although the distal end 116 has been illustrated as angled, such as is typical with needles, for at least one embodiment, the distal end 116 may be a solid or closed point, with the opening 120, such as a hole or slit, disposed just behind the solid end.

Moreover, in varying embodiments the first length L1 116 of the first needle 102 is at least one-and-a-half times the second length L2 122 of the second needle 104. Indeed, for at least one embodiment the first length L1 116 of the first needle 102 is at least twice the second length L2 122 of the second needle 104.

FIGS. 5A, 5B and 5C are annotations of enlarged drawings showing the base 106 for AFNA 100 as shown in FIG. 1A. Such a base 106 may be made by injection molding or casting of thermoplastic type materials so as to form the first end 108, the second end 110 and the sidewall 112 between the first end 108 and the second end 110. As the base 106 may be a generally solid piece of molded or carved material, save for the ports/channels providing liquid passage from the second needle 104 through the base 106 to the second end 110, and air passage from the vent 120 to the first needle 102, the sidewall 112 may actually be viewed as simply the side material comprising the base 106. As these enlarged figures help illustrate, for at least one embodiment the first needle 102 is disposed in a sleeve 500 that is connected to the side vent 120. The second needle 104 is disposed in a sleeve 502 that is connected to the second end 110, which has been also illustrated as a luer connector 504.

As noted above, for at least one embodiment, if the distal end 118 of the first needle 102 encounters the bottom 212 of the chamber 202, the first needle 102 can be pushed back into the base 106. This may be achieved by mounting the first needle 102 only partially within the first needle 102 receiving sleeve 500. For such an embodiment, if the bottom 212 of the chamber 202 is encountered the first needle 102 will be pushed further into the base 106 towards the vent 120. As may also be appreciated, the size of the vent 120 for this embodiment of AFNA 100 is such that a filter, one way valve, or both may be disposed in the vent 120.

Returning to FIGS. 1A, 1B and 1C, it will also be appreciated that for at least one embodiment a removable protective cap (not shown) is provided to protectively cover the first needle 102 and second needle 104. With respect to the embodiments of AFNA 100 as shown in FIGS. 1B and 1C, an end view of each is provided. In varying embodiments, the protective cap may be of a traditional style that snap fits about the base 106, or an Ergonomic Needle Protector as set forth in U.S. patent application Ser. No. 15/291,913, filed Oct. 12, 2016 and entitled System And Method for Ergonomic Needle Protector, incorporated herein by reference.

Moreover, to summarize, for at least one embodiment, provided is an AFNA 100 for avoiding foam generation when extracting a liquid 204 from a hollow vessel such as a vial 200 suitable for the containment of liquids 204, the vessel having a chamber 202 with a bottom 212 and opposite thereto an opening sealed with a penetrable and re-sealable stopper 208 providing an inner surface 214 above the chamber 202. This AFNA 100 includes a needle base 106 having a first end 108 and opposite thereto a second end 110 and a sidewall 112 there between. The second end 110 is structured and arranged for temporary connection to a syringe 300 having a barrel 302, a plunger 304 and an inner chamber 306. A first needle 102 having a hollow shaft and a first length L1 116 extends from the first end 108 to provide an open distal end 118 above the first end 108, the first needle 102 has a second end vented through the sidewall 112. A second needle 104 having a hollow shaft and a second length L2 122 extending from the first end 108 generally parallel to the first needle 102 to provide a distal end 124 above the first end 108 and below the distal end 118 of the first needle 102, the second needle 104 having a second end 110 in fluid communication with the second end 110 of the needle base 106. As noted, the first length L1 116 is pre-selected to place the distal end 118 of the first needle 102 proximate to the bottom 212 of the chamber 202 and the second length L2 122 is pre-selected to place the distal end 124 of the second needle 104 within the chamber 202 and proximate to the re-sealable stopper 208.

Yet another embodiment may be summarized as an AFNA 100 for avoiding foam generation when extracting a liquid 204 from a hollow vessel suitable for the containment of liquids, the vessel having a chamber 202 with a bottom 212 and opposite thereto an opening sealed with a penetrable and re-sealable stopper 208 providing an inner surface 214 above the chamber 202. This AFNA 100 includes a needle base 106 having a first end 108 and opposite thereto a second end 110 and a sidewall 112 there between. The second end 110 is structured and arranged for temporary connection to a syringe 300 having a barrel 302 and a plunger 304. A first needle 102 having a hollow shaft and a first length L1 116 extends from the first end 108 to provide an open distal end 118 above the first end 108, the first needle 102 has a second end 110 vented through the sidewall 112. A second needle 104 having a hollow shaft and a second length L2 122 at least half the first length L1 116 of the first needle 102 extends from the first end 108 generally parallel to the first needle 102 to provide a distal end 124 above the first end 108 and below the distal end 118 of the first needle 102, the second needle 104 having a second end 110 in fluid communication with the second end 110 of the needle base 106.

Changes may be made in the above methods, systems and structures without departing from the scope hereof. It should thus be noted, that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A method of avoiding foam generation when extracting a liquid from a hollow vessel suitable for the containment of liquids, the vessel having a chamber with a bottom and opposite thereto an opening sealed with a penetrable and re-sealable stopper providing an inner surface above the chamber, comprising:

inserting a first needle having a hollow shaft through the penetrable and re-sealable stopper to dispose a distal end of the first needle adjacent to the bottom of the chamber, a second end of the first needle remaining open outside the chamber;

inserting a second needle having a hollow shaft through the penetrable and re-sealable stopper to dispose a distal end of the second needle adjacent to the inner surface, a second end of the second needle connected to a syringe having a barrel with a plunger;

inverting the vessel, the distal end of the first needle now disposed adjacent to the upper most inner surface of the chamber; and activating the plunger to draw the liquid from the vessel through the second needle and into the barrel of the syringe, the first needle permitting air to be delivered into the vessel above the liquid being dispensed so as to minimize foaming of the liquid during extraction, wherein the first needle and the second needle are provided by a needle base having a first end and opposite thereto a second end and a sidewall there between, the second end structured and arranged for temporary connection to a syringe having a barrel and a plunger;

the first needle having a first length and the second needle having a second length, the first length and second length pre-determined such when the first needle and the second needle are inserted through the penetrable and re-sealable stopper, the distal end of the first needle is disposed adjacent to the bottom of the chamber and the distal end of the second needle adjacent to the inner surface of the penetrable and re-sealable stopper.

2. The method of claim 1, wherein the first needle is fitted with an air filter.

3. The method of claim 1, wherein the first needle is gated by a one way valve.

4. The method of claim 1, wherein the first needle is longer than the second needle.

5. The method of claim 1, wherein the first needle and the second needle are provided by a unified needle assembly connecting structured and arranged for removable attachment to a syringe.

6. The method of claim 1, wherein the distal end of the first needle provides an aperture that is obliquely angled.

7. The method of claim 1, wherein the distal end of the second needle provides an aperture that is obliquely angled.

8. The method of claim 1, wherein the distal end of the first needle provides at least one hole in the shaft.

9. The method of claim 1, wherein the distal end of the second needle provides at least one hole in the shaft.

10. The method of claim 1, further including the use of a plurality of second needles.

11. The method of claim 1, wherein in a first position prior to extraction of the liquid, the vessel has an air gap above the liquid and below the inner surface of the chamber, and in a second position after inversion, the air gap is disposed about the distal end of the first needle.

12. The method of claim 1, wherein the first needle and second needle are distinct separate structures extending from the needle base.

13. An anti-foaming needle assembly for avoiding foam generation when extracting a liquid from a hollow vessel suitable for the containment of liquids, the vessel having a chamber with a bottom and opposite thereto an opening sealed with a penetrable and re-sealable stopper providing an inner surface above the chamber, comprising:
  a needle base having;
    a first end and opposite thereto a second end and a sidewall there between, the second end structured and arranged for temporary connection to a syringe having a barrel and a plunger;
    a first needle having a hollow shaft and a first length extending from the first end to provide an open distal end above the first end, the first needle having a second end vented through the sidewall; and
    a second needle having a hollow shaft and a second length extending from the first end generally parallel to the first needle to provide, when inverted, a distal end above the first end and below the distal end of the first needle, the second needle having a second end in fluid communication with the second end of the needle base;
  wherein the length of the first needle and the length of the second needle are pre-determined such that when the first needle and the second needle are inserted through the penetrable and re-sealable stopper, the distal end of the first needle is disposed adjacent to the bottom of the chamber and the distal end of the second needle adjacent to the inner surface of the penetrable and re-sealable stopper.

14. The anti-foaming needle assembly of claim 13, wherein the first needle is fitted with an air filter.

15. The anti-foaming needle assembly of claim 13, wherein the first needle is gated by a one way valve.

16. The anti-foaming needle assembly of claim 13, wherein the first needle is a telescoping structure, extending from a stowed position towards the first length when released.

17. The anti-foaming needle assembly of claim 13, wherein the first needle is a telescoping structure, structured and arranged to compress back upon itself.

18. The anti-foaming needle assembly of claim 13, wherein the first needle is in sliding connection with the needle base such that it may partially slide into the needle base.

19. The anti-foaming needle assembly of claim 13, wherein the first needle is flexible.

20. The anti-foaming needle assembly of claim 13, wherein the first needle is longer than the second needle.

21. The anti-foaming needle assembly of claim 13, wherein the first needle and the second needle are provided by a unified needle assembly connecting structured and arranged for removable attachment to a syringe.

22. The anti-foaming needle assembly of claim 13, wherein the distal end of the first needle provides an aperture that is obliquely angled.

23. The anti-foaming needle assembly of claim 13, wherein the distal end of the first needle provides at least one hole in the shaft.

24. The anti-foaming needle assembly of claim 13, wherein the second end of the needle base is a Luer fitting.

25. The anti-foaming needle assembly of claim 13, further including a removable cap structured and arranged to protectively cover the first and second needles.

26. The anti-foaming needle assembly of claim 13, wherein the first needle and the second needle share a common sidewall.

27. The anti-foaming needle assembly of claim 13, wherein the first needle and the second needle are combined components of a compound needle structure collectively enclosing the hollow shaft for each needle for about the length of the second needle.

28. The anti-foaming needle assembly of claim 13, wherein the first needle and second needle are distinct separate structures extending from the needle base.

* * * * *